United States Patent [19]

Imanaka et al.

[11] Patent Number: 5,068,194

[45] Date of Patent: Nov. 26, 1991

[54] BACILLUS STEAROTHERMOPHILUS STRAIN HAVING A HIGH PROTOPLAST FORMING RATIO

[75] Inventors: Tadayuki Imanaka, Suita; Shoji Sakurai, Shizuoka, both of Japan

[73] Assignee: Nikko Bio Technica Co., Ltd., Shizuoka, Japan

[21] Appl. No.: 256,584

[22] Filed: Oct. 12, 1988

[30] Foreign Application Priority Data

Oct. 12, 1987 [JP] Japan .................................. 62-256965

[51] Int. Cl.$^5$ ................................................ C12N 1/20
[52] U.S. Cl. .................................. 435/252.5; 435/832
[58] Field of Search .................. 435/74, 252.31, 252.5, 435/832

[56] References Cited

U.S. PATENT DOCUMENTS 4,695,546 9/1987 Aiba et al. ............................ 435/320

OTHER PUBLICATIONS

Bergey's Manual of Systemic Bacteriology, vol. 2, 1984, pp. 1104–1138.
Chen, Z. et al., Genetic Analysis of *Bacillus stearothermophilus* by Protoplast Fusion, *J. Bac.*, vol. 165, No. 3, pp. 994–1001, 1986.
Aiba, S. et al., Cloning and Expression of Thermostable Amylase from *Bacillus Sterothermophlus* in *Bacillus Stearothermophilus* and *Bacillus subtilus*, *Applied & Environmental Microbiol.*, vol. 46(5), pp. 1059–1065 1983.

*Primary Examiner*—Douglas W. Robinson
*Assistant Examiner*—Marian C. Knode
*Attorney, Agent, or Firm*—Bacon & Thomas

[57] ABSTRACT

A novel strain belonging to *Bacillus stearothermophilus*. The strain of the present invention has a protoplast-forming ratio of not less than 99% and has a ration of regeneration of cell wall of not less than 50%, and is transformable with a plasmid.

3 Claims, No Drawings

BACILLUS STEAROTHERMOPHILUS STRAIN HAVING A HIGH PROTOPLAST FORMING RATIO

BACKGROUND OF THE INVENTION

I. Field of the Invention

This invention relates to a novel strain of *Bacillus stearothermophilus*. The novel strain belonging to *B. stearothermophilus* of the present invention can be used as a host for producing enzymes or other useful substances by means of genetic engineering techniques.

II. Description of the Related Art

In general, production of useful substances such as enzymes by thermophilic bacteria has the following advantages:

(1) Since the bacteria are cultured at a high temperature, contamination by other bacteria hardly occurs.

(2) Since the rate of proliferation is high, the productivity is high.

(3) Since the bacteria can be cultured at a high temperature, the cost for cooling the fermentation system is reduced.

Thus, if a thermophilic bacterium from which protoplast can be easily formed and which can easily be transformed is obtained, it can advantageously be used for the production of useful substances as a host by means of genetic engineering technique.

SUMMARY OF THE INVENTION

Accordingly, the object of the present invention is to provide a novel thermophilic bacterium from which protoplast can be easily formed and which can easily be transformed by plasmid DNA.

The present inventors found and isolated a novel thermophilic bacterium belonging to *Bacillus stearothermophilus* from feces of a Thoroughbred horse to complete the present invention.

The present invention provides a novel strain belonging to *Bacillus stearothermophilus*, which has a protoplast-forming ratio of not less than 99% and has a ratio of regeneration of cell wall of not less than 50%, and which is transformable with plasmid.

The strain of the present invention has a very high protoplast-forming ratio and a ratio of regeneration of cell wall. Thus, the strain of the present invention is very useful as a host for producing useful substances such as enzymes by transforming the host with a recombinant plasmid encoding the useful substance.

DETAILED DESCRIPTION OF THE PREFERRED EMBODIMENTS

As stated above, the novel strain belonging to *Bacillus stearothermophilus* of the present invention has a protoplast-forming ratio of not less than 99%. The term "protoplast-forming ratio" herein means the percentage of the cells which form protoplasts by the treatment with lysozyme according to a conventional method (Imanaka et al., *J. Bacteriol.* vol. 149, No. 3, pp. 824-830 (1982)). The *B. stearothermophilus* strain of the present invention also has a ratio of regeneration of cell wall of not less than 50%. The term "ratio of regeneration of cell wall" herein means the percentage fo the protoplasts which regenerate their cell wall when the protoplasts are treated according to the conventional trasformation method (so called protoplast method) (Imanka et al., supra).

The *B. stearothermophilus* strain of the present invention can be cultured in the minimal medium (1.4% $K_2HPO_4$, 0.2% $(NH_4)_2SO_4$, 0.1% sodium citrate, 0.02% $MgSO_4=H_2O$, 0.5% glucose).

The *B. stearothermophilus* strain of the present invention may preferably be cultured at a temperature of 50-60° C. and at a pH of 5.7-8, in the minimal medium (addition of thyamine hydrochloride (5 μg/ml) to the minimal medium enhances cell proliferation), L medium (1% peptone, 0.5% yeast extract, 0.5% NaCl, pH 7.2), or in the 2L medium (content of each component except for NaCl is twice that of the L medium).

EXAMPLES

The present invention will now be described by way of the examples thereof.

EXAMPLE 1

Isolation of *Bacillus stearothermophilus* SI1

From feces of Thoroughbred horses, bacteria were taken and each of them was cultured at 55° C. on the L agar medium (tryptone or peptone 10 g/l, yeast extract 5 g/l, NaCl 5 g/l, agar 15 g/l, pH 7.2) to obtain a single colony of each of the bacteria. Various characteristics of each of the bacteria forming the colonies were checked. Among these, a bacterium which had a protoplast-forming ratio of not less than 99.9% and has a ratio of regeneration of cell wall of about 70-80% was found. The bacterium was named *Bacillus stearothermophilus* SI1, and was deposited with Fermentation Research, Institute of Japan (FRI) under the accession number of FERM BP-3102 on Oct. 1, 1987.

Characteristics of *Bacillus stearothermophilus* SI1

The *B. stearothermophilus* SI1 has the following characteristics:

(1) It has sporogenesis.
(2) It does not grow anaerobically.
(3) It produces catalase.
(4) Glucose Fermentation:
   It produces acid but does not produce gas in glucose fermentation.
(5) Growing pH
   at pH 5.7: grows
   at pH 5: does not grow
(6) Growing Temperature
   at 70° C.: does not grow
   at 65° C.: grows
   at 50° C.: grows
   at 45° C.: grows
   at 40° C.: does not grow
(7) Enzyme Production
   Amylase: −
   Protease: −
   Pullulanase: +
   xylanase: ±
   cellulase: ±
   lipase: +
(wherein − means no production, + means production and ± means slight production)
(8) Drug Resistance
   Streptomycin (Sm, 100 μg/ml): resistant
   Kanamycin (Km, 25 μg/ml): sensitive
   Erythromycin (Em, 10 μg/ml): sensitive
   Tetracycline (Tc, 25 μg/ml): sensitive
   Ampicillin (Ap, 25 μg/ml): sensitive
   Chloramphenicol (Cm, 25 μg/ml): sensitive Cephalospolin (Cp, 25 μg/ml): resistant (9) It has a potential plasmid (20 ±1 Md).

(10) It is Gram-positive.

(11) It can grow in the minimal medium.

(12) It shows the maximum population density ($OD_{660}$) of 7.8 (the absorbance at 660 nm after 8-hours'culture at 60° C., pH 7.2 in 100 ml of 2L medium contained in a 500 ml flask).

Among the characteristics as described above, from the fact that (a) it grows at 65° C., (b) it grows at pH 5.7 but does not grow at pH 5.0, (c) it is absolute aerobic, (d) it forms spores, (e) it is Gram-positive, and (f) it produces catalase, the bacterium was identified as belonging to *Bacillus stearothermophilus* in accordance with the "Bergey's Manual of Systematic Bacteriology" vol. 2.

EXAMPLE 2

In accordance with a conventional method (T. Imanaka et al., *J. Bacteriol*. vol. 149, No. 3, pp. 824–830 (1982), which is hereby incorporated by reference), *Bacillus stearothermophilus* SI1 was transformed by the protoplast method. The protoplast method basically comprises the steps of (1) forming protoplasts by the treatment with lysozyme in a hypertonic solution, (2) transferring a plasmid DNA into the protoplasts under the existence of polyethylene glycol, and (3) regenerating the cell walls of the protoplasts.

The plasmids used were pUB110 ($Km^r$), pTB913 ($Km^r$), pTB90 ($Km^r$) and pTB53 ($Km^r$, $Tc^r$) (T. Imanaka et al., *J. Gen. Microbiol*. vol. 130, pp. 1399–1408 (1984)).

As a result, the protoplast-forming ratio of *B. stearothermophilus* SI1 was as high as not less than 99.9%, and the ratio of regeneration of cell wall was as high as about 70–80%. This ratio of regeneration is very high when compared with those of the other thermophilic bacteria. Further, utilizing the $Km^r$ marker, the efficiency of transformation was checked. As a result, as many as about $10^6$ transformants were obtained using 1 μg of DNA.

EXAMPLE 3

Production of Neutral Protease Using *B. stearothermophilus* SI1 as Host

*B. stearothermophilus* SI1 was transformed in the same manner as in Example 2 with a plasmid pTZ232 ($Km^r$, $Tc^r$, Npr+) which encodes neutral protease and which gives resistance to kanamycin and tetracycline (M. Kubo et al., *Journal of General Microbiology*, 134, 1883–1892 (1988)). As a control, *Bacillus stearothermophilus* CU21 (T. Imanaka et al., *Journal of Bacterilogy*, 149 824–830 (1982)) was transformed in the same manner with the same plasmid.

The colonies of the transformants as described above and untransformed *B. stearothermophilus* SI1 were formed on the L agar medium containing 1% casein, and the size of the halos formed was examined (M. Fujii et al., *Journal of Bacteriology*, 154, 831–837 (1983)). The larger the amount of the neutral protease produced, the larger the diameter of the halo formed. In this experiment, the *B. stearothermophilus* SI1 transformed with pTZ232 formed a halo about three times larger than that of the *B. stearothermophilus* CU21, and the untransformed SI1 did not form a halo. These results show that the *B. stearothermophilus* SI1 of the present invention is excellent as the host for the production of useful substances by the transformation with a plasmid encoding the useful substance.

EXAMPLE 4

Production of Alpha Amylase Using *B. stearothermophilus* SI1 as Host

*B. stearothermophilus* SI1 was transformed in the same manner as in Example 2 with a plasmid pAT5 ($Km^r$, $Tc^r$, Amy+) which encodes amylase and which gives resistance to kanamycin and tetracycline (S. Aiba et al., *Applied and Environmental Microbiology*, 46, 1059–1065 (1983); R. Nakajima et al., Journal of Bacteriology, 163, 401–406 (1985)). As a control, *Bacillus stearothermophilus* CU21as mentioned above was transformed in the same manner with the same plasmid.

The colonies of the transformants as described above and untransformed *B. stearothermophilus* SI1 were formed on the L agar medium containing 1% soluble starch, and iodine solution was added to the medium. The size of the halos formed was examined. The larger the amount of the amylase produced, the larger the diameter of the halo formed. In this experiment, the *B. stearothermophilus* SI1 transformed with pAT5 formed a halo about three times larger than that of the *B. stearothermophilus* CU21, and the untransformed SI1 did not form a halo. These results also show that the *B. stearothermophilus* SI1 of the present invention is excellent as the host for the production of useful substances by the transformation with a plasmid encoding the useful substance.

We claim:

1. A substantially pure culture of *Bacillus stearothermophilis* FERM BP-3102.

2. A substantially pure culture of *Bacillus stearothermophilus* according to claim 1, which is cultured at a temperature of between 50° and 60° C.

3. A substantially pure culture of *Bacillus stearothermophilus* according to claim 1 which is cultured in minimal medium, wherein the minimal medium comprises 1% peptone, 0.5% yeast extract and 0.5% NaCl.

* * * * *